US012773325B2

(12) United States Patent
Collier

(10) Patent No.: US 12,773,325 B2
(45) Date of Patent: Oct. 27, 2026

(54) HARD LINER REMOVAL INSTRUMENT

(71) Applicant: Joint Development, Inc., Salt Lake City, UT (US)

(72) Inventor: Thomas Collier, Park City, UT (US)

(73) Assignee: Joint Development, Inc., Salt Lake City, UT (US)

( * ) Notice: Subject to any disclaimer, the term of this patent is extended or adjusted under 35 U.S.C. 154(b) by 391 days.

(21) Appl. No.: 18/222,971

(22) Filed: Jul. 17, 2023

(65) Prior Publication Data

US 2024/0016626 A1 Jan. 18, 2024

Related U.S. Application Data

(60) Provisional application No. 63/389,638, filed on Jul. 15, 2022.

(51) Int. Cl.
*A61B 17/46* (2006.01)
*A61F 2/46* (2006.01)

(52) U.S. Cl.
CPC .......... *A61F 2/4609* (2013.01); *A61F 2/4603* (2013.01); *A61F 2002/4619* (2013.01)

(58) Field of Classification Search
CPC .................. A61F 2/4609; A61F 2/4603; A61F 2002/4619; A61B 17/92; A61B 2017/925
See application file for complete search history.

(56) References Cited

U.S. PATENT DOCUMENTS

| | | | | |
|---|---|---|---|---|
| 5,741,268 A * | 4/1998 | Schutz | A61B 17/0642 | 606/104 |
| 5,938,701 A * | 8/1999 | Hiernard | A61F 2/4637 | 623/22.21 |
| 2018/0125474 A1* | 5/2018 | Dougherty | A61B 17/00234 | |
| 2019/0388243 A1* | 12/2019 | Furore | A61F 2/4609 | |
| 2020/0217370 A1* | 7/2020 | Finke | F16B 21/18 | |

* cited by examiner

*Primary Examiner* — Amy R Sipp
(74) *Attorney, Agent, or Firm* — Lowry Blixseth APC; Scott M. Lowry

(57) ABSTRACT

A hard liner removal instrument includes a barrel containing a striking mass in slidable relation therewith and a spring positioned between a first end of the barrel and the striking mass. The spring selectively moves between a normal resting position and a loaded position where the striking mass is positioned a greater distance from a second end of the barrel opposite the first end than when the spring is in the normal resting position. As such, movement of the spring from the loaded position to the normal resting position accelerates the striking mass into the second end of the barrel to generate an impulse sufficient to interrupt a Morse taper to remove one orthopedic component from another, e.g., during revision surgery.

14 Claims, 12 Drawing Sheets

HARD LINER REMOVAL INSTRUMENT

BACKGROUND OF THE INVENTION

The present invention generally relates to a hard liner removal instrument. More specifically, the present invention is directed to a hard liner removal instrument having a loadable spring designed to accelerate a mass into contact with an impactor that translates an impulse within an acetabular prosthesis to cause disengagement of the hard liner.

Total hip arthroplasty ("THA") is a surgical procedure where the hip joint is replaced by a prosthetic implant known, e.g., as a hip prosthesis, and may be performed for purposes of relieving arthritis pain or to help with a hip fracture. More specifically, THA typically involves replacing the acetabulum and the femoral head, such that the patient effectively receives a new artificial ball-and-socket joint. One type of hip prosthesis uses a dual mobility acetabular component that includes an acetabular cup implanted into the natural hipbone socket, and a hard liner that engages the acetabular cup in friction-fit engagement, such as by way of a Morse taper. The Morse taper ensures the hard liner remains substantially stationary relative to the acetabular cup after implantation. The hard liner includes an inner concave surface designed to receive an outer convex surface of a polymer insert, and the polymer insert includes an inner concave surface designed to receive a smooth and at least partially rounded femoral head that is able to rotate relative thereto.

While THA involving dual mobility acetabular components are increasingly common and successful operations, residual problems remain. Surgeon error can lead to improper alignment of the dual mobility acetabular components and/or defective implantation. Furthermore, the concave surface of the hard liner, the outer convex surface and/or inner concave surface of the polymer insert, and/or the outer convex surface of the femoral head are all articulatory surfaces subject to wear over time, occasionally resulting in the need for replacement. Additionally, micromotions between the acetabular cup and the hard liner can cause undesired wear/corrosion due to, e.g., friction, galling, and/or fretting. The undesired wear/corrosion on either the hard liner or the acetabular cup decreases the flexural rigidity of the hip prosthesis and, in some cases, can lead to fractures. While use of materials that polish well, such as metal or metal alloys (e.g., titanium, cobalt chromium, etc.), plastic polymers, or ceramics (e.g., zirconia toughed alumina) have reduced failures due to wear/corrosion, joint implant components are still subject to failure from time-to-time.

When any defect or failure occurs, hip revision surgery may be required to repair or replace the existing defective hip prosthesis. Hip revision surgery can involve removing one or more of the implanted acetabular cup, the hard liner, polymer insert, and/or the femoral head. In particular, while the Morse taper desirably facilitates friction-fit engagement between the hard liner and the acetabular cup after implantation, such friction-fit engagement also increases the difficulty in removing the hard liner from the acetabular cup in hip revision surgery. One current practice to remove the hard liner from the acetabular cup involves locating a punch on the rim of the acetabular cup, and striking the punch with a hammer to create an impulse that causes the hard liner to dislodge from the acetabular cup. Skill is required to locate the punch on the acetabular cup, then position the upwardly projecting punch in an orientation suitable for striking, and then hold the punch in place so that it can be accurately struck with the hammer. Since it is difficult to remove the hard liner after one strike, this two-handed process often requires repeatedly striking the punch with the hammer. As such, this process is both strenuous on the surgeon and undesirably time-consuming. The hammer and punch are also relatively large and bulky surgical instruments that increase the overall size, number, and mass of the required instruments to complete hip revision in an already crowded surgical space. Furthermore, the high impact force created by the hammer is imprecise and can create other undesired issues during THA given that it is a relatively low precision instrument.

Current attempts to simplify the removal of the hard liner from an acetabular cup during hip revision have been largely unsuccessful in satisfying the need for a smaller and more easily controllable and repeatable hard liner removal tool having a higher degree of accuracy. In one example prior art device, U.S. Pat. No. 8,936,604, the contents of which are herein incorporated by reference in its entirety, discloses a pneumatic surgical instrument for extracting joint components. While the pneumatic device replaces the need to use the inefficient and bulky hammer and punch approach, it is overly complex and requires a gas source to create a pneumatic impulse. The complexity of this device also increases manufacturing and assembly costs. Additionally, the cost and time to re-sterilize complex surgical instruments before use in subsequent procedures is also typically relatively higher than smaller, simpler surgical instruments. As such, the pneumatic device disclosed in the '604 patent increases the overall costs to perform the surgery since hospitals experience higher costs to acquire, process, and sterilize such a device prior to, during, and post-surgery. Moreover, because gas cartridges create the pneumatic impulse, the number of impulses may be limited by the volume of gas in each cartridge. As such, numerous cartridges may need to be sterilized and delivered to the operating room for any given surgery.

There exists, therefore, a significant need in the art for a hard liner removal instrument having a spring-activated handle that accelerates a movable mass into engagement with an axially aligned impactor upon spring recoil to generate an impulse thereon that translates into and disrupts the Morse taper that otherwise retains the hard liner and acetabular cup in friction-fit engagement with one another, thereby permitting removal of the hard liner from the acetabular cup during, e.g., revision surgery. The present invention fulfills these needs and provides further related advantages.

SUMMARY OF THE INVENTION

In one embodiment, a hard liner removal instrument as disclosed herein may include a striking mass and an impactor generally axially aligned with the striking mass and in spaced apart relation relative thereto. A spring coupled to a portion of the striking mass at one end and coupled to a portion of the impactor at another end may be selectively movable from a normal resting position to a loaded position offsetting the striking mass a greater distance from the impactor than when the spring is in the normal resting position. Here, movement of the spring from the loaded position to the normal resting position accelerates the striking mass into contact with the impactor. This generates an impulse at the impactor that translates into an orthopedic implant for purposes of interrupting a Morse taper so one implant component can be removed from another during revision surgery. In this respect, the impactor may have a mass ratio range of 1-to-5 to 1-to-15 relative to the striking mass to ensure the impulse is sufficient to interrupt the Morse taper while minimizing translation of the impulse into the patient.

The striking mass may include an outwardly extending pommel having a plurality of external corrugations formed therein that provides enhanced grip during use. Moreover, the impactor may also include a tapered head and include a circumferential recess positioned above the tapered head to accommodate engagement with the spring. The spring may include an external tension spring having an internal diameter relatively larger than an external diameter of the striking mass for slide on engagement therewith. Here, the striking mass may also include a contact head having a chamfered leading edge designed to generally slide over one or more of a plurality of coils that form the spring. When in the normal resting position, the contact head may abut or otherwise be positioned near a strike surface of the impactor, which may have a curved surface, a spherical surface, or a spheroidal surface.

The striking mass may include a circumferential recess having a size and shape to accommodate engagement with the spring. Moreover, the striking mass may also have an outwardly projecting flange positioned above the circumferential recess. Here, the outwardly projecting flange may have an external diameter relatively larger than an outer diameter of the spring, which effectively prevents the spring from moving further up along the striking mass during use. In one embodiment, for surgeries requiring more precision, the impactor may have an outwardly extending pinhead tip having a relatively consistent outer diameter thinner than the striking mass. In alternative embodiments, the impactor may also include one or more slip-resistant corrugations notched therein to provide enhanced grip during use. In one embodiment, the impactor may have a mass of 10-30 grams and the striking mass may have a mass of 50-450 g. In more specific embodiments, the impactor may have a mass of approximately 12-22 grams and the striking mass may have a mass of approximately 75-250 grams. The spring actuating movement of the striking mass relative to the impactor may be a mechanical spring, a magnetic spring, or a solenoid.

In another embodiment as disclosed herein, a hard liner removal instrument may include a barrel containing a striking mass in slidable relation therewith. Here, a spring positioned between a first end of the barrel and the striking mass may be selectively movable between a normal resting position and a loaded position where the striking mass is positioned a greater distance from a second end of the barrel opposite the first end than when the spring is in the normal resting position. As such, movement of the spring from the loaded position to the normal resting position accelerates the striking mass into the second end of the barrel to generate the aforementioned impulse sufficient to interrupt a Morse taper to dislodge one orthopedic implant component relative to another.

In these embodiments, the spring may be an internal compression spring positioned between the striking mass and at least one retaining shoulder inwardly projecting into the barrel. The striking mass may be loaded against the spring by way of an externally accessible handle having a rod extending generally coaxially into the barrel and through the spring and an aperture in the striking mass. The rod may then terminate in a stopper relatively larger than the aperture in the striking mass. This permits using the externally accessible handle to retract the rod within the barrel to compress the striking mass against the spring. In one embodiment, the aperture may be a two-stage chamber having a first relatively wider channel of a size and shape to selectively receive the stopper therein, which is positioned in front of a second channel relatively smaller than the stopper while being of sufficient size and shape for pass-through reception of the rod. Here, the first relatively wider channel and the second channel define a shoulder in between where the stopper seats when moving the spring from the normal resting position to the loaded position.

In another aspect of these embodiments, the striking mass may include a circumferential indentation selectively slidably engageable with a spring-biased release lever. As such, the rod is selectively independently movable relative to the striking mass and selectively independently movable relative to the spring when the spring-biased release lever is engaged with the circumferential indentation of the striking mass. A trigger spring positioned within a trigger housing may normally bias the release lever through an aperture in the barrel a sufficient distance to engage at least a portion of the circumferential indentation when aligned therewith. The release lever may include a leading edge selectively slidable relative to a chamfered edge of the striking mass during movement of the spring from the normal resting position to the loaded position. As such, the release lever may further include an outwardly flaring base slidably engaged with a pair of sloped shoulders extending thereover and movable relative thereto by an externally accessible trigger. Accordingly, the actuating the lever effectively removes the release lever out from engagement with the circumferential indentation to activate acceleration of the striking mass within the barrel in accordance with the embodiments disclosed herein.

In some embodiments, the internal compression spring may be a size and shape to extend substantially along a length of the barrel when in the normal resting position. In these embodiments, the spring may extend the striking mass out from one end of the barrel and be designed to contact the orthopedic implant component receiving the aforementioned impulse.

Alternatively, the hard liner removal instrument may include an impactor housing having a notch selectively coupled with a retaining clip seated on an outwardly projecting step of the barrel. In these embodiments, the impactor housing may include an enclosure having a size and shape for select reception of a front end of the barrel. An impact spring seated within the enclosure between an inner wall thereof and the front end of the barrel may soften or dampen the impulse translated from the striking mass to the impactor in these embodiments. The impact spring may have, e.g., a thickness of 1-5 millimeters ("mm") depending on the desired dampening of the impulse. Moreover, the impactor housing may also extend out and over the front end of the barrel to form a rearwardly facing exhaust channel therewith. This provides a rearward exit for fluid (e.g., air) in front of the striking mass to escape when the striking mass moves from the loaded position and the normal resting position. Such a rearward exit ensures that the air pushed out from the hard liner removal instrument is back and away from the open wound.

In another embodiment as disclosed herein, the striking mass may include a loading projection having a size and shape to at least partially extend into a loading channel of a rotatable actuator. Here, the loading channel is movable by the rotatable actuator between an engagement position for select sliding interaction with the loading projection and a disengagement position out from select sliding interaction with the loading projection. When in the disengagement position, the rotatable actuator is movable independent of the striking mass along a length of the barrel. Moreover, when in the loaded position, the spring biases a chamfered projection into forward engagement in blocking relationship with a release lever to ensure the striking mass does not reaccelerate down the barrel. In one embodiment, once released by the release lever, the striking mass may travel down the length of the barrel into contact with an impactor positioned at the second end of the barrel. In one embodiment, the impactor may include a tapered head having a tip forming an outwardly projecting ledge, and the tapered head may at least partially extend out from the barrel for contact with an orthopedic implant component.

In another embodiment, the hard liner removal instrument may include a spring-activated handle that accelerates a moveable mass into engagement with an axially aligned impactor upon spring recoil to generate an impulse thereon that translates into at least one orthopedic prothesis component to facilitate removal thereof during revision surgery.

In another embodiment, the hard liner removal instrument may include an external extension spring having a first end coupled to handle and a second end coupled to an impactor. The handle may further include a striking mass concentric within the spring that includes a contact head with a chamfered leading edge designed to facilitate pass-through movement of the striking mass within the external extension spring during use. The impactor may further include a strike surface opposite the impactor tip positioned to be impacted by the contact head of the striking mass. Moreover, the impactor may include a taper terminating in an impactor tip selectively locatable on a rim of an acetabular cup. In this respect, in use, the handle is retracted away from the impactor to extend the external extension spring. The handle is subsequently released whereby the external extension spring recoils, thereby accelerating the striking mass forward such that the contact head strikes the strike surface of the impactor to generate an impulse that translates to the rim of an acetabular cup in the form of a pulse that vibrates free the Morse taper otherwise locking the acetabular cup to the hard liner in friction-fit engagement therewith.

In an alternative embodiment, to provide an enhanced grip, the handle may further include a generally diametrically enlarged pommel having a plurality of ridges or steps formed along a tapered section that transitions into the relatively smaller diameter handle. The first end of the external extension spring may couple to a first circumferential recess in the impactor and the second end of the external extension spring may couple to a second circumferential recess in the handle. The handle may further include a flange extending out therefrom to help prevent the spring from extending past the second circumferential recess. The impactor tip may be in the form of a relatively elongated pinhead tip having a relatively consistent outer diameter. Alternatively, the impactor tip and/or the handle may further include a plurality of corrugations designed to selectively engage a surgical clamp.

In an alternative embodiment, a trigger-based hard liner removal instrument may include an elongated barrel with an impactor tip coupled to one end, a movable mass contained within the barrel, and an internal compression spring designed to selectively accelerate a movable mass within the barrel to generate the aforementioned impulse at the impactor tip. More specifically, the trigger-based hard liner removal instrument may include a pullback actuator having a relatively enlarged first end disposed within the barrel, an elongated rod concentric within the internal compression spring, and a second end that includes an externally accessible handle. In this respect, the relatively enlarged first end is of a size and shape for select reception and movement within a first relatively wider channel of a two-stage hollow chamber formed within the movable mass, while a shoulder formed from the transition between the relatively wider chamber and a relatively narrower chamber formed therebehind provides surface-to-surface engagement with the enlarged first end for purposes of enabling the pullback actuator to reposition the movable mass into a loaded position compressing the internal compression spring. A trigger housing downwardly coupled to the barrel may include a trigger spring that biases a release lever into select engagement with the movable mass, to hold the movable mass in the loaded position. Once loaded, the pullback actuator may slide forward within the barrel without dislodging the movable mass from the loaded position. The trigger housing may further include a downwardly projecting trigger able to selectively disengage the release lever from the movable mass, whereby the internal compression spring is then able to extend forward to accelerate the movable mass down the length of the barrel and into contact with the impactor tip, to generate the aforementioned impulse.

In another aspect of these embodiments, the impactor tip may include an impactor housing extending over the outside of the barrel and retained thereon via a retaining ring. An impact spring may separate the end of the barrel from the impactor tip and be designed to soften the impact the movable mass therein. As such, the impactor head is able to move relative to the barrel. Moreover, the impactor tip may further include an outwardly projecting ledge to assist the surgeon in locating the impactor tip on the rim of the acetabular cup, such as by way of dual surface engagement therewith. Alternatively, the movable mass may include a downwardly projecting chamfered projection and a downwardly projecting loading projection that selectively engage the release lever. In this embodiment, a rotatable actuator may include a loading channel that selectively engages the loading projection to allow the rotatable actuator to pull the movable mass into the loaded position. Once loaded, rotating the rotatable actuator may selectively disengage the rotatable actuator from the loading projection of the movable mass, thereby allowing the movable mass to accelerate out from the loaded position without interference from the rotatable actuator once actuated by the trigger. In other embodiments, a grip may couple to the barrel and a trigger guard may couple to the trigger housing.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 4:
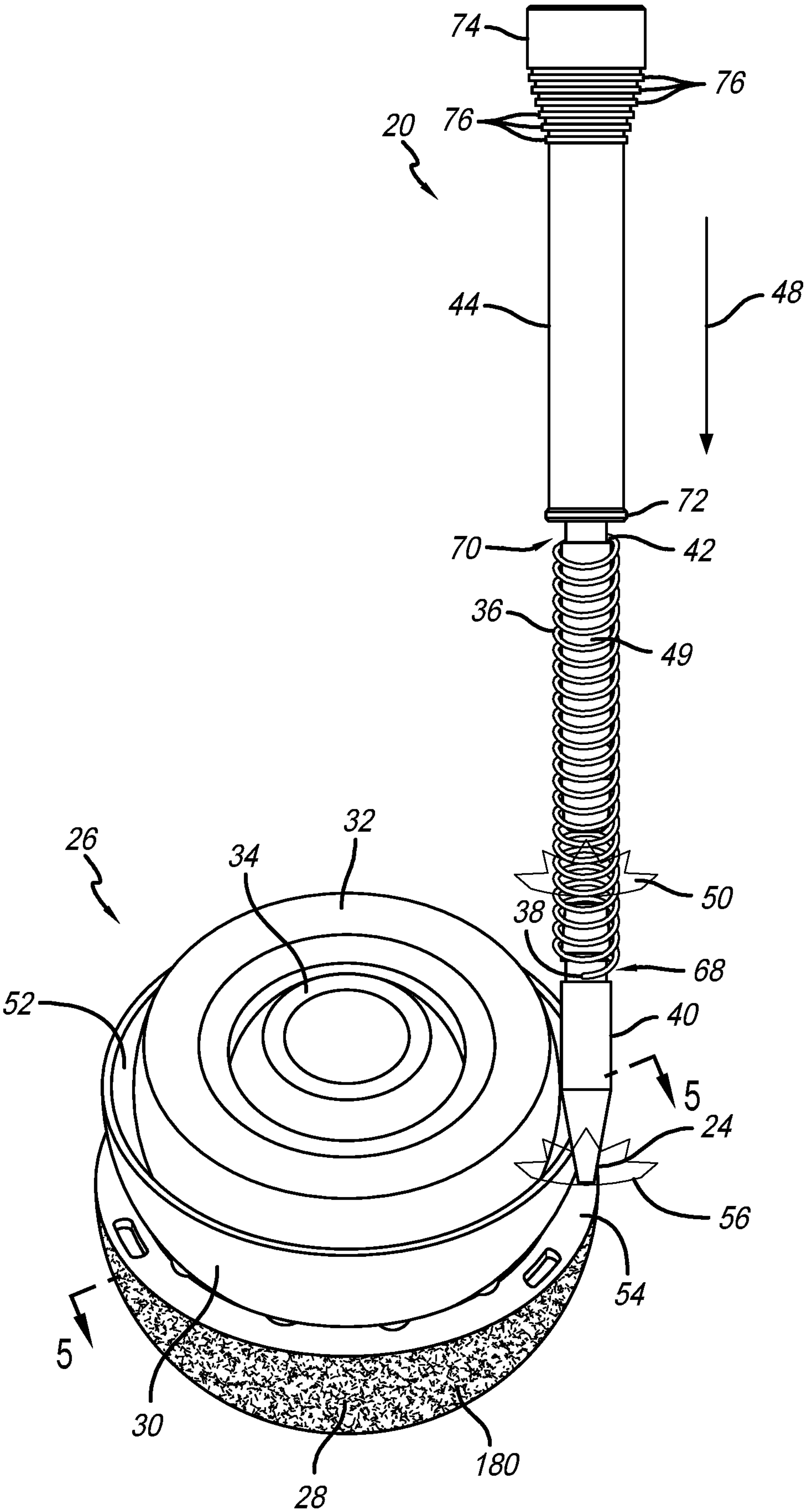
FIG. 4 is a perspective view of the hard liner removal instrument after release of the tensioned handle from the extended position in FIG. 3, further illustrating impaction of the striking mass with the impactor to generate an impulse that translates to a rim of an acetabular cup.
Figure 5:
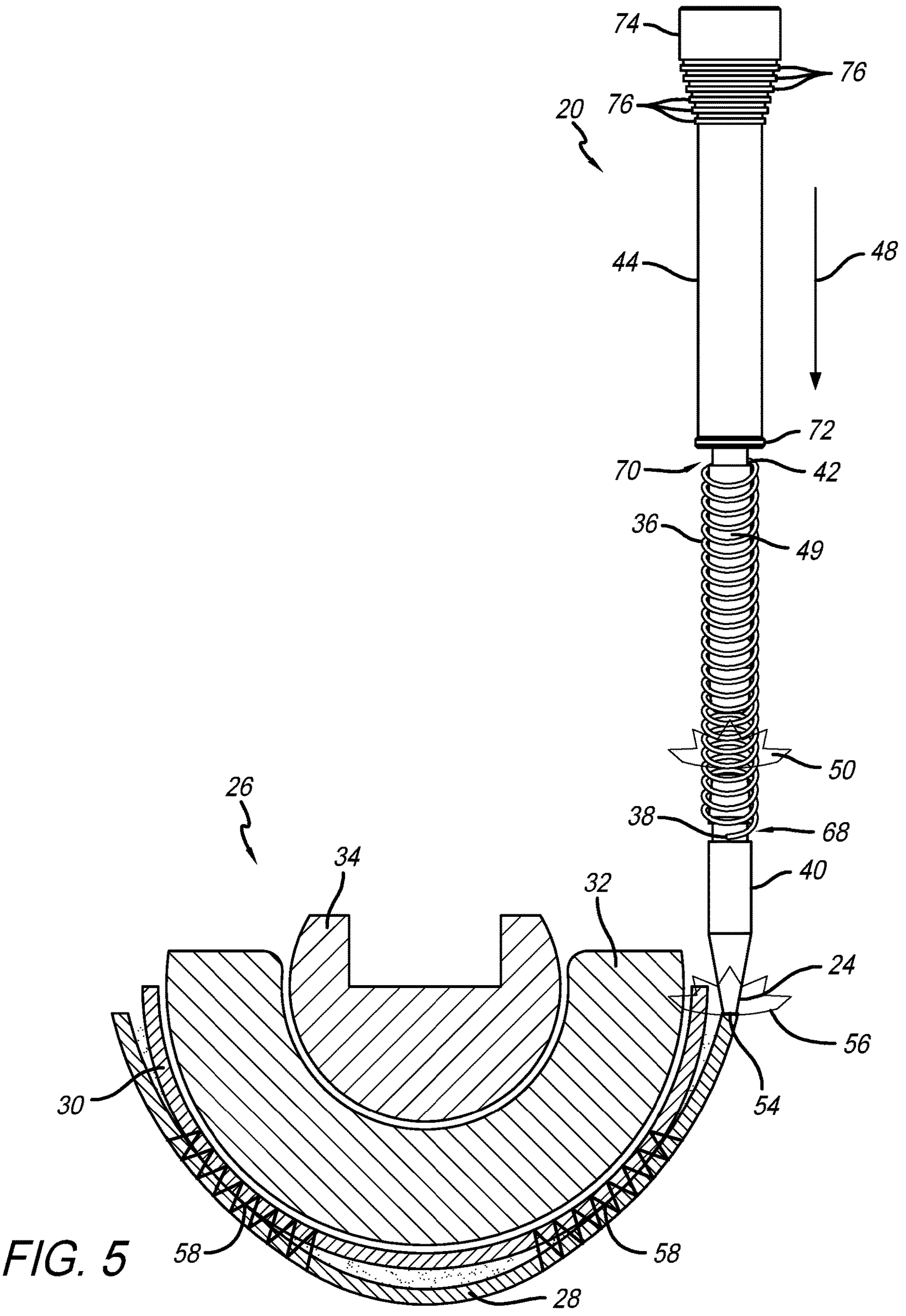
FIG. 5 is a cross-sectional view taken about the line 5-5 in FIG. 4, further illustrating the impulse disrupting the Morse taper between a hard liner and the acetabular cup, thereby allowing the hard liner to snap out from friction-fit engagement with the acetabular cup.

As shown in the exemplary drawings for purposes of illustration, various embodiments of a hard liner removal instrument are disclosed herein, including with respect to a hard liner removal instrument 20 as illustrated, e.g., in FIGS. 1-7, and an alternative embodiment of a trigger-based hard liner removal instrument 22 as illustrated in FIGS. 8-13 and 16-17. In general, the hard liner removal instruments 20, 22 are designed to allow a surgeon to locate an impactor tip 24 on, and apply an impulse to, at least one component of an orthopedic prosthesis, such as a dual mobility acetabular prosthesis 26 having an acetabular cup 28, a hard liner 30, a polymer insert 32, and/or a femoral head 34 as illustrated in FIGS. 4-5. For example, the impactor tip 24 may be placed against the acetabular cup 28 in a manner where the hard liner removal instrument 20, 22 may apply an impulse thereto designed to dislodge the hard liner 30 therefrom by causing a disruption in a Morse taper that otherwise maintains press-fit engagement between the acetabular cup 28 and hard liner 30. While the hard liner removal instruments 20, 22 are designed to typically dislodge the hard liner 30 with a single impulse, as discussed in more detail below, the hard liner removal instruments 20, 22 are also designed to be able to quickly and easily repeatedly apply accurate pointed impulses in localized areas of the dual mobility acetabular prosthesis 26 to dislodge any of the components (e.g., one or more of the acetabular cup 28, the hard liner 30, the polymer insert 32, and/or the femoral head 34) that may be stuck or need dislodging during revision surgery.

For example, in one embodiment as illustrated in FIGS. 1 and 3-7, each of the hard liner removal instruments 20, 20', 20" include an external extension spring 36 (e.g., a mechanical spring, a magnetic spring, and/or a solenoid) captured along the length thereof between a bottom end 38 that couples to an impactor 40 and a top end 42 that couples to a handle 44. As best illustrated from FIG. 3 to FIGS. 4 and 5, the surgeon may operate the hard liner removal instrument 20 by holding the impactor 40 and pulling the handle 44 away, such as in the direction of an arrow 46 illustrated in FIG. 3. This extends the external extension spring 36 into an activated and tensioned position. Upon releasing the handle 44, the external extension spring 36 recoils back to its normal unloaded position illustrated in FIG. 1 and, in doing so, the extension spring 36 pulls the handle 44 toward the impactor 40 along the direction of arrow 48 illustrated, e.g., in FIGS. 4 and 5. The spring 36 should be of a size, shape, and material (e.g., thickness and tension) such that its strength causes an internally located striking mass 49 to remain substantially coaxial with the impactor 40 upon extension, and to accelerate the striking mass 49 to a speed sufficient to strike the impactor 40 with enough force to generate an impulse 50 that translates through the impactor tip 24 and into the desired component upon recoil when returning from its un-tensioned position illustrated in FIG. 1.

More specifically, and as briefly mentioned above, the hard liner 30 typically couples with the acetabular cup 28 by way of a Morse taper that ensures the hard liner 30 remains engaged with the acetabular cup 28 after implantation. Moreover, in the dual mobility acetabular prosthesis 26 illustrated in FIGS. 4-5, the femoral head 34 selectively couples to the polymer insert 32, and the polymer insert 32 is also of a size and shape for select reception within an inner concave surface 52 (FIG. 4) of the hard liner 30 to permit rotational movement therein. While the femoral head 34 and/or polymer insert 32 are typically easily removable from one another and/or the hard liner 30 (e.g., as a result of being rotatable relative to one another), the Morse taper between the hard liner 30 and acetabular cup 28 helps ensure that each remain in press-fit engagement with one another. While this may be preferred to maintain the structural integrity of the prosthesis 26 after implantation, it significantly increases the difficulty in removing the hard liner 30 from the acetabular cup 28 during revision surgery.

As such, the hard liner removal instruments 20, 22 are designed to dislodge the hard liner 30 from the acetabular cup 28 by way of the above-mentioned impulse 50 that effectively disrupts the Morse taper that otherwise holds the hard liner 30 in friction fit engagement with the acetabular cup 28. More specifically in this respect, in one embodiment, the surgeon may locate the impactor tip 24 of the hard liner removal instrument 20 on a rim 54 of the acetabular cup 28, and then pull the handle 44 away from the impactor 40 thereby extending the external extension spring 36 and the striking mass 49 thereunder, as briefly mentioned above. When the surgeon releases the handle 44, the spring 36 recoils and pulls the striking mass 49 into contact with the impactor 40 to create the impulse 50 illustrated in FIGS. 4-5. As such, the impulse 50 translates through the impactor 40 to the impactor tip 24, and into the acetabular cup 28 and/or the hard liner 30 as indicated by a pulse 56. The pulse 56 then reverberates through the material of the acetabular cup 28 and/or the hard liner 30 causing a vibration 58 that disrupts the Morse taper. Doing so should cause the hard liner 30 to dislodge from the acetabular cup 28. If a single impulse 50 happens not to dislodge the hard liner 30 on the first try, the surgeon may easily and quickly repeat the process by simply retracting the handle 44 again while maintaining the impactor tip 24 against the rim 54 of the acetabular cup 28. There is no need to realign a punch and/or hammer, or to potentially refill a pneumatic surgical instrument with a new cartridge, since the hard liner removal instrument 20 is usable in a single two-handed (i.e., the hard liner removal instrument 20) or one-handed (i.e., the trigger-based hard liner removal instrument 22) design.

The impactor 40 may include a taper 60 that decreases the width or diameter of the impactor 40 into the relatively narrower or smaller impactor tip 24. Doing so provides a larger surface area for the surgeon to hold the impactor 40 while, at the same time, allowing the surgeon to more specifically locate the impactor tip 24 within a relatively small or tight location where the surgery is being performed so that the pulse 56 can be applied to a specific section of the rim 54. As such, in cases where the impactor tip 24 needs to be located within a relatively small surgical opening, the surgeon may hold the impactor 40 above the taper 60, and extend the impactor tip 24 further down into the surgical opening than where the surgeon needs to hold the impactor 40. The sloping nature of the taper 60 may also help facilitate slide-in reception of the impactor tip 24 into the surgical opening. As such, once located in the desired position on the rim 54, the surgeon is able to effectuate application of the impulse 50 and/or the pulse 56 while holding the impactor 40 above the taper 60.

Figure 1:
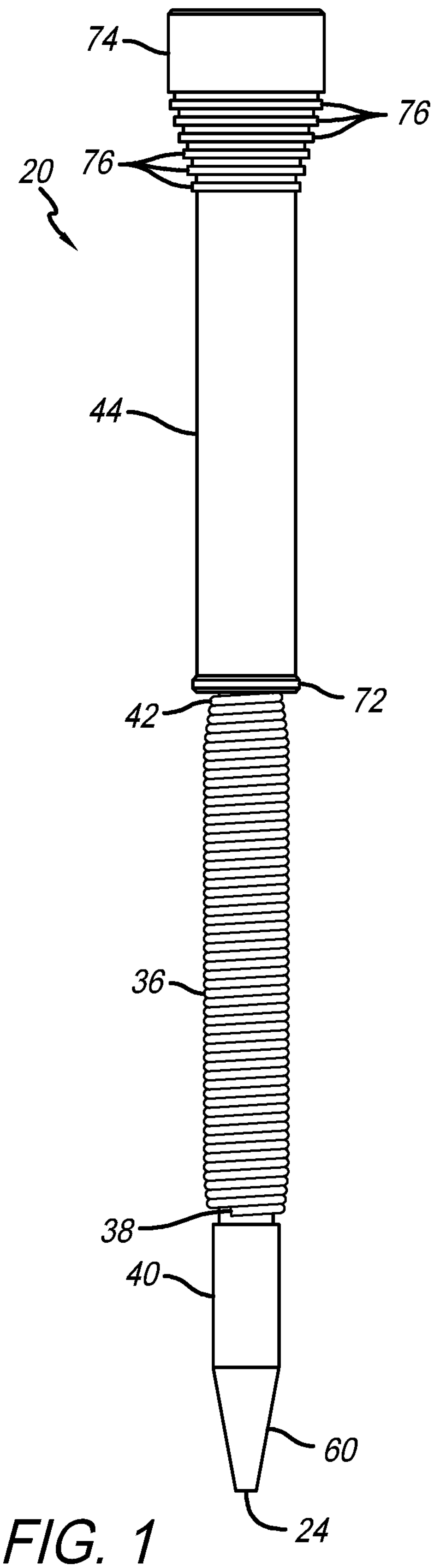
FIG. 1 is a perspective view of one embodiment of a hard liner removal instrument having a handle axially aligned with an impactor and movable relative thereto by way of an external extension spring.
Figure 2:
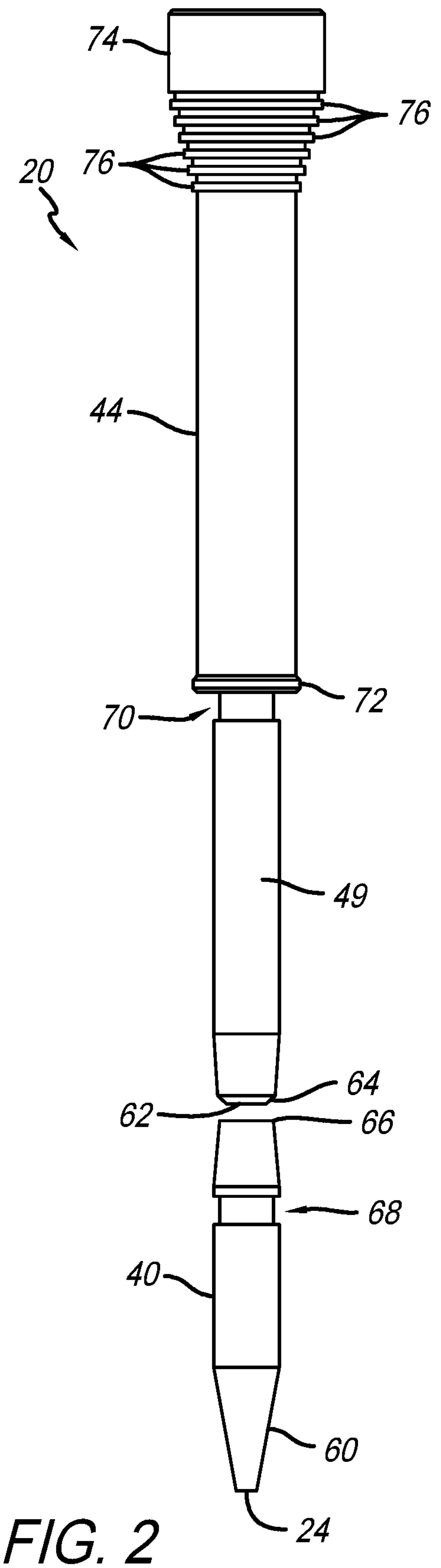
FIG. 2 is perspective view of the hard liner removal instrument to FIG. 1 without the external extension spring, further illustrating a striking mass extending out from the handle and axially aligned with a strike surface of the impactor.
Figure 3:
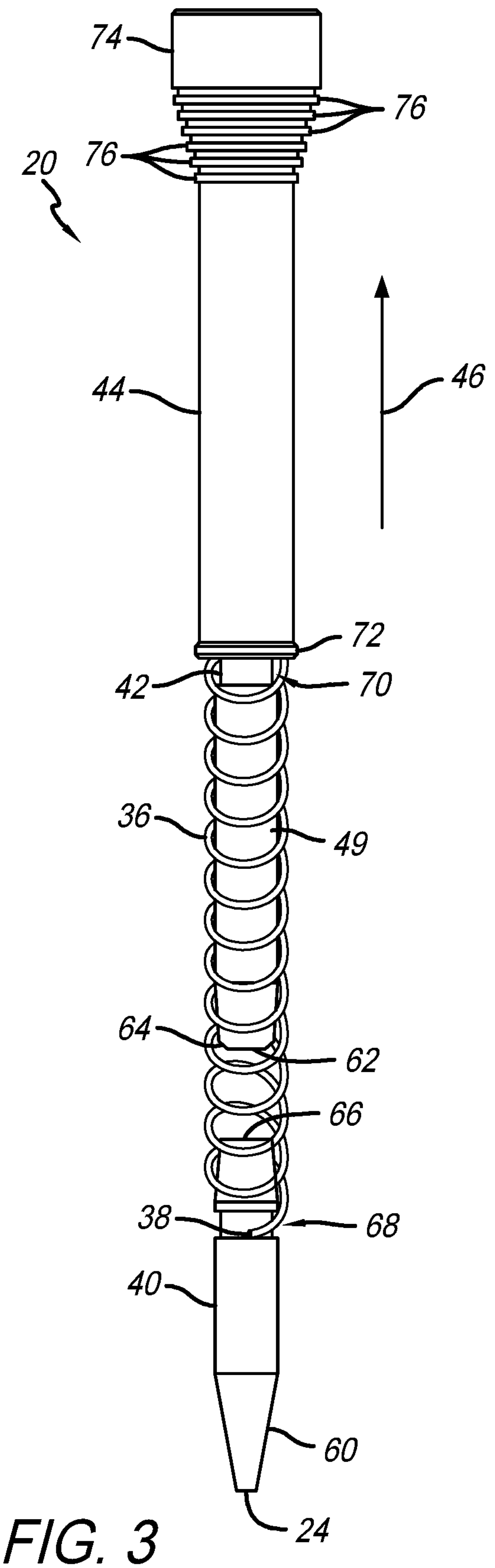
FIG. 3 is an alternative perspective view of the hard liner removal instrument of FIGS. 1-2, further illustrating the handle in an extended position tensioning the extension spring.

As best illustrated in FIG. 2, the striking mass 49 includes a contact head 62 having a chamfered leading edge 64 designed to facilitate movement of the striking mass 49 within the interior of the extension spring 36. That is, while the spring 36 may be of a size, shape, and material (e.g., thickness and tension) wherein its strength causes the internally located striking mass 49 to remain substantially coaxial with the impactor 40 upon extension, the chamfered leading edge 64 provides a ramped surface that allows the striking mass 49 to more smoothly flow over one or more of the coils in the extension spring 36 during return travel, should the striking mass 49 come into contact with one or more of the coils by virtue of becoming somewhat off-center within the external extension spring 36. To this end, such guided movement of the striking mass 49 within the external extension spring 36 generally directs the contact head 62 into alignment with a strike surface 66 (best illustrated in FIG. 2) that provides a generally flat surface area where the contact head 62 of the striking mass 49 can impact the impactor 40. The planar surfaces of the contact head 62 and the strike surface 66 provide an enhanced surface area where the striking mass 49 can contact the impactor 40 to generate the desired impulse 50. In alternative embodiments, the strike surface 66 may include a curved strike surface, a spherical strike surface, a spheroidal strike surface, or the like.

The impactor 40 may further include a circumferential recess 68 generally disposed between the taper 60 and the strike surface 66 that allows the bottom end 38 of the external extension spring 36 to couple thereto. In one embodiment, the circumferential recess 68 may be of a depth sufficient to receive one or more of the coils at the bottom end 38 of the external extension spring 36, such as in flush engagement therewith. Similarly, the handle 44 may include a similarly shaped circumferential recess 70 positioned immediately above the striking mass 49, of which may be of a size and shape to selectively receive one or more coils at or near the top end 42 of the external extension spring 36, such as in flush engagement therewith. Flush engagement, e.g., may maintain the overall width or diameter of the hard liner removal instrument 20 consistent with the impactor 40 and/or the handle 44. Additionally, the handle 44 may further include an outwardly projecting flange 72 positioned above the circumferential recess 70 to better assist in preventing or resisting movement of the spring 36 past the circumferential recess 70.

Figure 6:
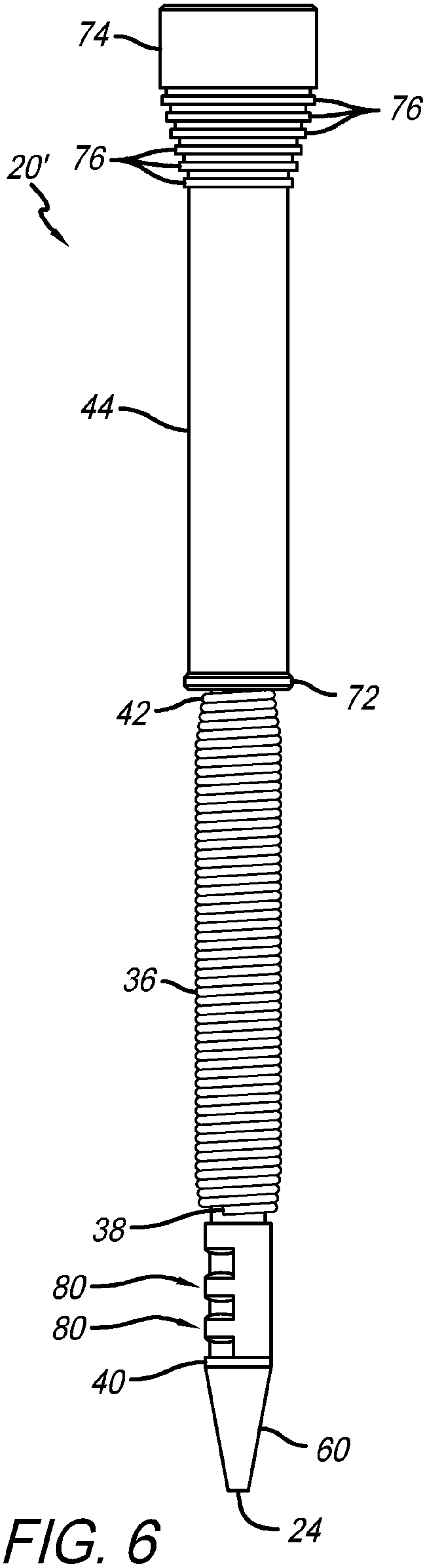
FIG. 6 is a perspective view of an alternative hard liner removal instrument, illustrating the impactor having a set of externally accessible corrugations.
Figure 7:
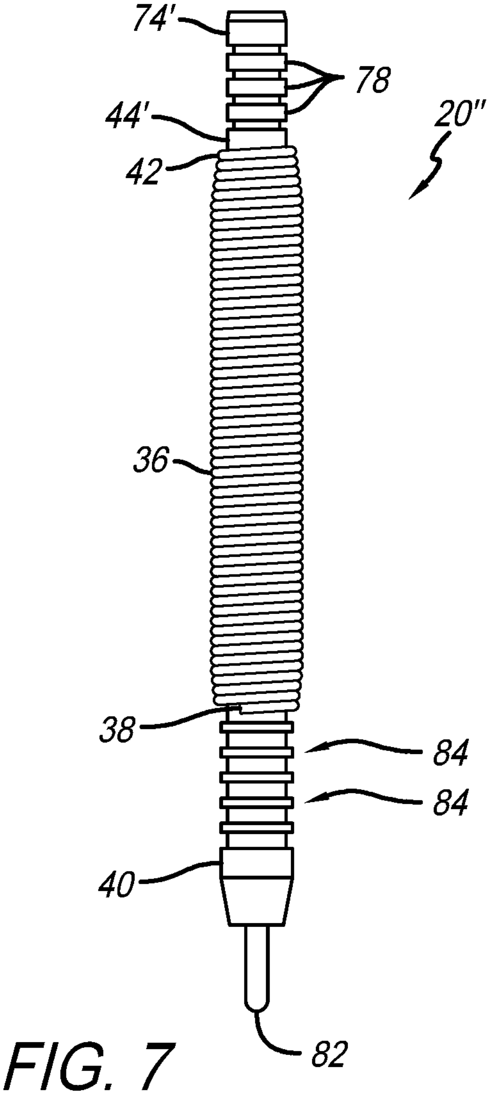
FIG. 7 is a perspective view of another hard liner removal instrument, illustrating the impactor having a pin-head and a set of alternative externally accessible corrugations.

In one embodiment, the handle 44 may also include a generally larger diameter pommel 74 at one end thereof opposite the impactor 40, of which generally tapers inwardly into the handle 44 as illustrated in FIGS. 1-6. Further, FIGS. 1-6 illustrate that the pommel 74 may also include a plurality of steps or ridges 76 formed along its taper to provide an enhanced grip for the surgeon during use of the hard liner removal instrument 20, 20'. That is, the steps or ridges 76 are formed in a manner to provide a series of progressively larger diameter edges upon which the surgeon can grip the handle 44. Naturally, such steps or ridges 76 help prevent the hard liner removal instrument 20, 20' from slipping out from within the grip of the surgeon. Moreover, in an alternative embodiment, FIG. 7 illustrates an alternative pommel 74' having an external diameter about the same size as its handle 44. Here, the plurality of ridges 76 may be replaced with a set of corrugations 78 formed from the body of the handle 44, which may similarly provide enhanced friction for gripping the hard liner removal instrument 20" along the length of the handle 44.

Non-slip features similar to the plurality of ridges 76 and/or the plurality of corrugations 78 may also be incorporated into the impactor 40. More specifically, in an alternative embodiment as illustrated in FIG. 6, the impactor 40 is illustrated including a plurality of corrugations 80 formed into the body of the impactor 40. Here, the plurality of corrugations are designed to provide enhanced non-slip grip of the impactor 40 by the surgeon. Moreover, the plurality of corrugations 80 may also be suitable for select reception and engagement of a surgical clamp (not shown). In some embodiments, a surgical clamp may optionally be used during surgery to better provide one-handed operation of the hard liner removal instrument 20, 20"; and/or so that the surgeon can operate the hard liner removal instrument 20, 20', 20" without the needed to actually reach into the surgical area.

FIG. 7 further illustrates an alternate embodiment wherein the impactor 40 may include a pinhead tip 82 having a relatively consistent outer diameter relatively longer and thinner than the substantially flat impactor tip 24. The size and shape of this tip 82 may be used in higher space constraint surgeries where there may be a desire (or need) to position the pinhead tip 82 on the rim 54 of the acetabular cup 28 in a more specific location, or at a relatively higher position, to effectuate generation of the impulse 50 with relatively minimal disruption to the surrounding tissue at the site of the surgery. In this embodiment, the impactor 40 may include a plurality of corrugations 84 formed between the bottom end 38 where the external extension spring 36 couples thereto and where the impactor 40 transitions to the pinhead tip 82. The plurality of corrugations 84 may be of a similar size and shape similar to the plurality of corrugations 78 formed from the handle 44' so as to provide better non-slip grip or for use in connection with a surgical clamp (not shown). Moreover, in this embodiment, the handle 44' may also be somewhat shorter and relatively thinner in diameter than the handle 44 disclosed above with respect to FIGS. 1-6, so as to further facilitate use in smaller spaces.

In another aspect of the embodiments illustrated with respect to FIGS. 1-7, the impactor 40 may have a mass relatively lower than that of the striking mass 49 to attain the desired impulse 50 sufficient to safely and effectively remove the hardliner from the acetabular cup. Specifically, in one embodiment, the impactor 40 may have a mass of approximately 10-30 grams ("g") and the striking mass 49 may have a mass of approximately 50-450 g. In an alternative embodiment, the impactor 40 may be approximately 12-22 g and the striking mass 49 may be approximately 75-250 g. In one specific embodiment, the impactor 40 may have a 12 g mass and the striking mass 49 may have a 120 g mass. As such, the ratio of the mass of the impactor 40 to the striking mass 49 may be anywhere from 1 to 5 to 1 to 15. The effect is that the striking mass 49 is able to accelerate to generate a force upon the relatively lower mass impactor 40 that translates a localized impulse spike that reverberates substantially into the surrounding orthopedic implant material, and not the patient. This is different than known prior art devices such as center punch tools because the impact tips of the center punch tools are too light relative to the striking mass used therewith whereby the ratio therebetween is on the order of 1 to 1 to 1 to 2. This results in a relatively high impulse and low impact force designed for driving wood screws or nails into wood, which is wholly unable to generate the type of force sufficient to safely and effectively dislodge a hardliner from an acetabular cup.

Figure 8:
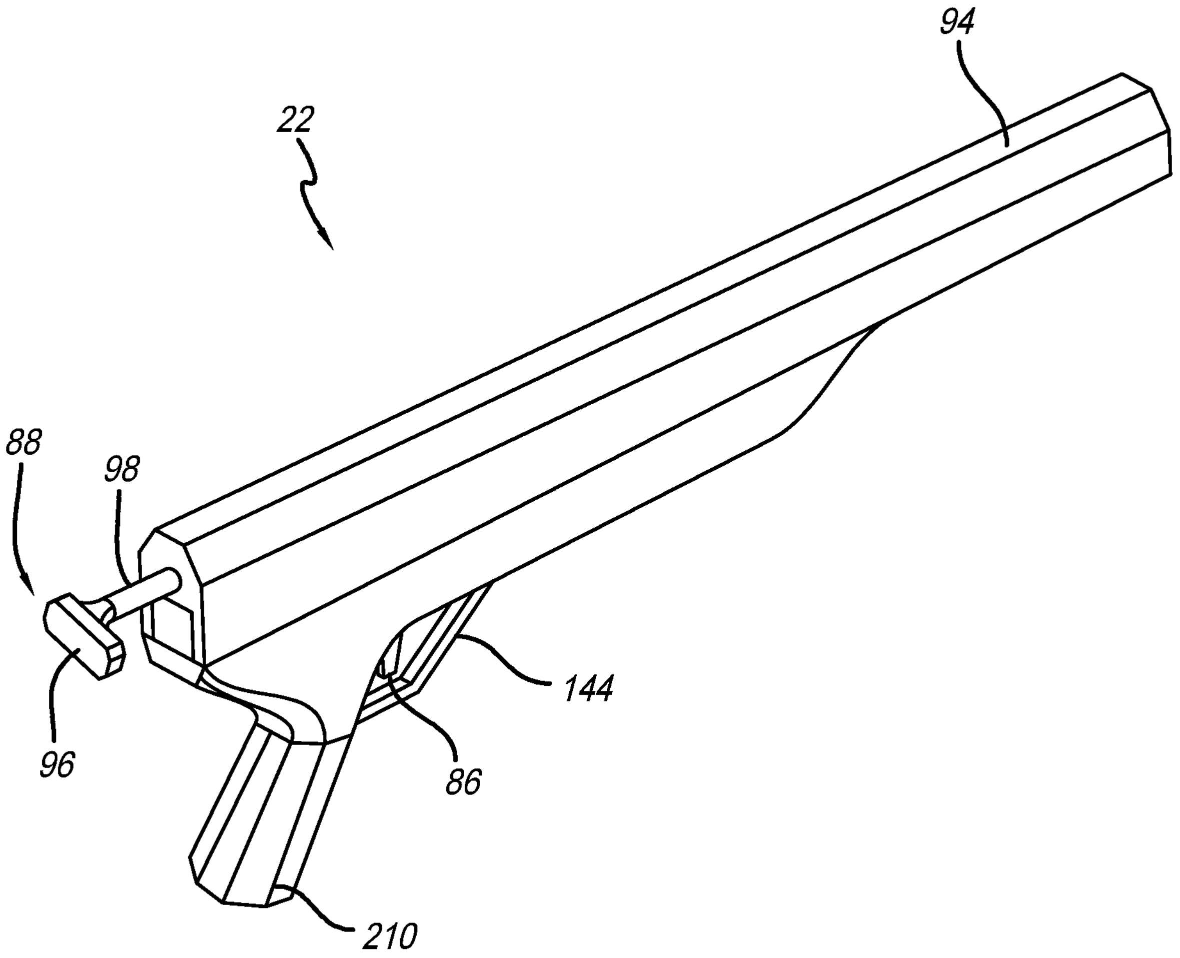
FIG. 8 is a perspective view of a trigger-based hard liner removal instrument having a pullback actuator operable by a trigger to release a movable mass down a length of a barrel.
Figure 9:
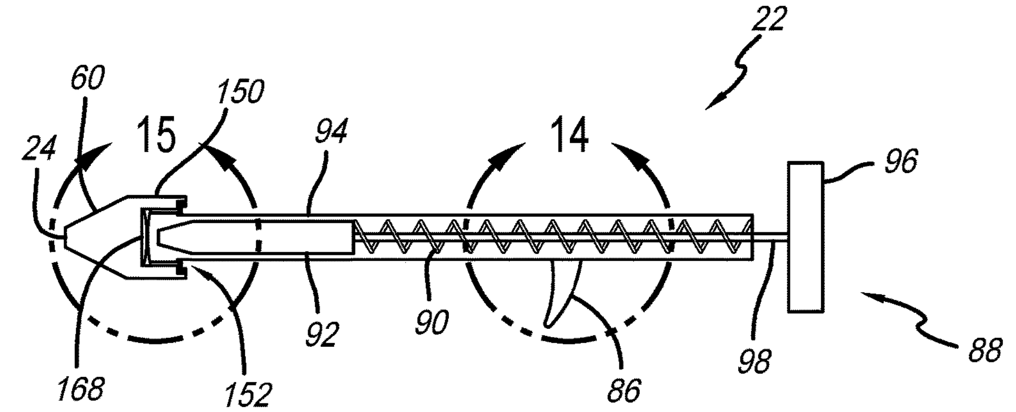
FIG. 9 is a perspective view of the trigger-based hard liner removal instrument in a normal resting position.

In an alternative embodiment, FIGS. 8-13 more specifically illustrate that the trigger-based hard liner removal instrument 22 includes a trigger 86 that operates in conjunction with a pullback actuator 88 and an internal compression spring 90 to accelerate a movable mass 92 within a barrel 94 for purposes of generating the impulse 50 at the impactor tip 24 (FIG. 13), similar to that disclosed above with respect to the hard liner removal instrument 20. More specifically as illustrated in FIG. 9, while the trigger-based hard liner removal instrument 22 is at rest in an unloaded position, the internal compression spring 90 contained within the barrel 94 is in an extended position generally biasing the movable mass 92 down the length of the barrel 94 near the impactor tip 24. Here, the pullback actuator 88 is in a normal resting position.

Figure 10:
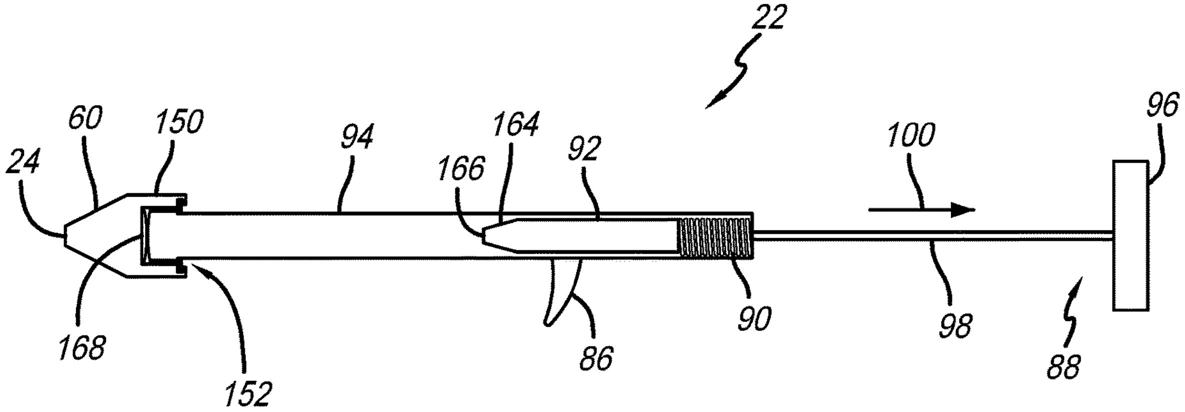
FIG. 10 is a perspective view of the trigger-based hard liner removal instrument of FIG. 9, further illustrating retraction of the movable mass by the pullback actuator into a loaded position compressing an internal compression spring.
Figure 11:
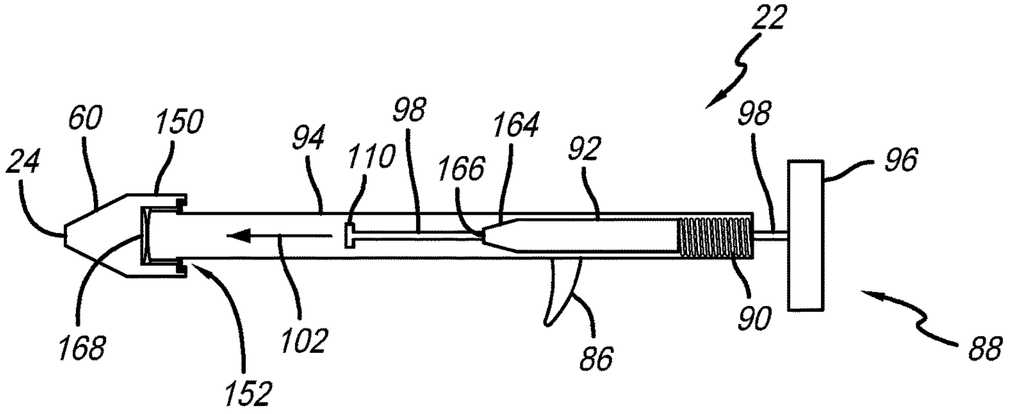
FIG. 11 is another perspective view of the trigger-based hard liner removal instrument of FIGS. 9 and 10, further illustrating return of the pullback actuator to its resting position illustrated in FIG. 9, while the movable mass and the internal compression spring remain in the loaded position.
Figure 12:
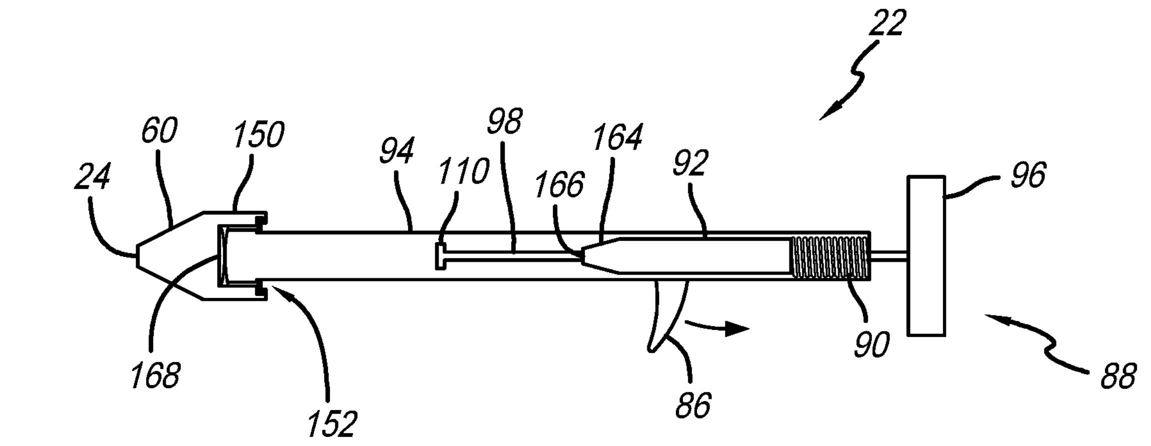
FIG. 12 is a perspective view of the trigger-based hard liner removal instrument, further illustrating actuating the trigger to release the movable mass.
Figure 13:
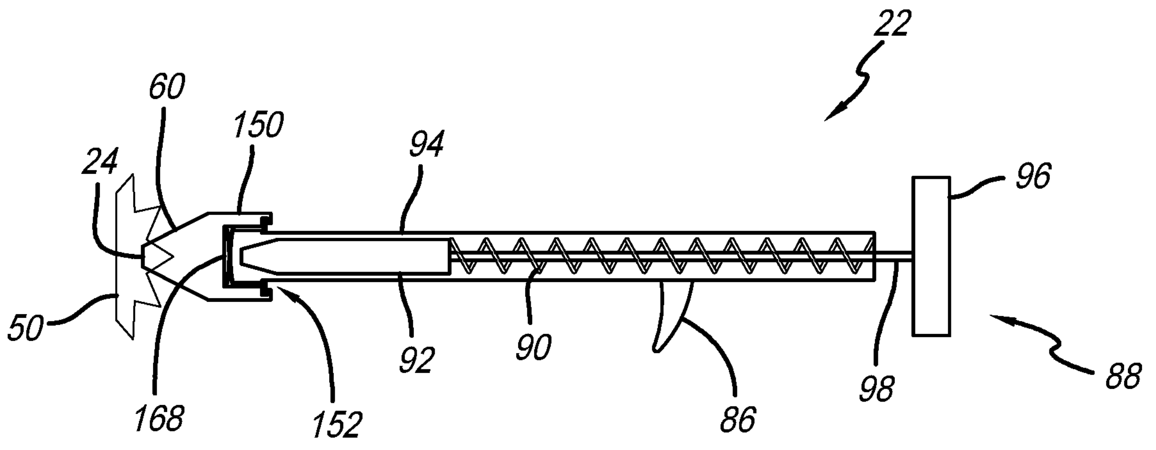
FIG. 13 is a perspective view of the trigger-based hard liner removal instrument similar to FIG. 12, further illustrating the internal compression spring extending down the length of the barrel to drive the movable mass into contact with the impactor, thereby generating the impulse.

The pullback actuator 88 includes an enlarged externally accessible handle 96 coupled to one end of a rod 98 that extends into the barrel 94 and is configured to operate movement of the movable mass 92 from the unloaded position illustrated in FIG. 9 to a loaded position illustrated, e.g., in FIGS. 10-12. In this respect, the externally accessible handle 96 provides the surgeon an enhanced surface area to grip and manipulate movement of the pullback actuator 88. The rod 98 may be generally positioned concentric within the barrel 94 and the internal compression spring 90, and be of a length substantially commensurate with the length of the barrel 94 to permit pull-back engagement with the movable mass 92 from the unloaded position illustrated in FIG. 9 to the loaded position illustrated, e.g., in FIG. 10.

As best illustrated in FIG. 10, the surgeon may grip the handle 96 to retract the pullback actuator 88 away from the actuator tip 24 along directional arrow 100. Doing so retracts the movable mass 92 within the barrel 94 and compresses the internal compression spring 90 as a result. Continued retraction of the movable mass 92 against the internal compression spring 90 eventually causes the movable mass 92 to engage the trigger 86, wherein the movable mass 92 is held in the loaded position illustrated in FIGS. 10-12. Once the movable mass 92 is locked in place with the trigger 86, the pullback actuator 88 is free to move independent of the movable mass 92, such as along directional arrow 102 and back to its normal resting position illustrated in FIG. 11, all without causing the movable mass 92 to disengage the trigger 86.

Figure 14:
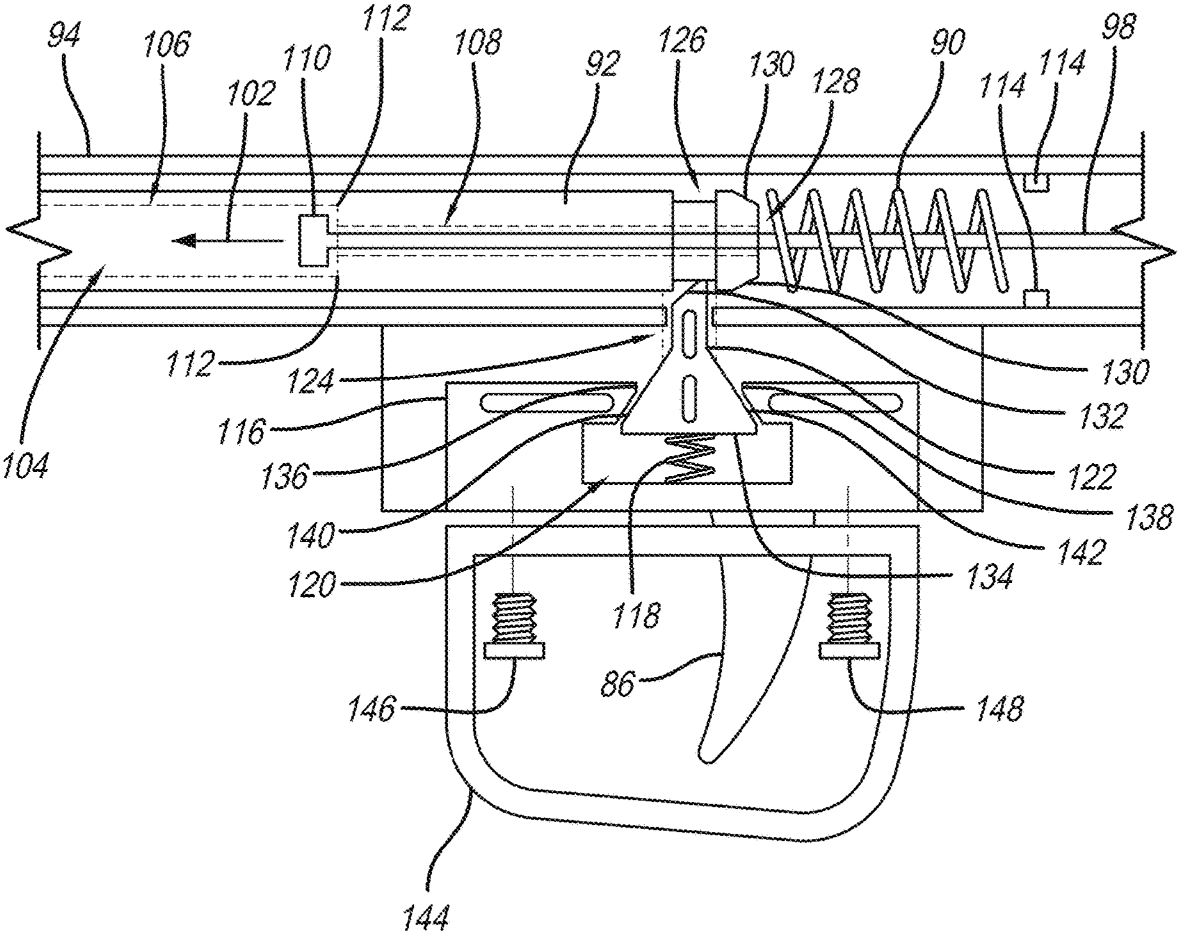
FIG. 14 is an enlarged perspective view taken about the circle 14 in FIG. 9, more specifically illustrating forward engagement of a release lever with a notch in the movable mass for retainment therein when the trigger-based hard liner removal instrument is in the loaded position.

More specifically, as illustrated in FIG. 14, once the movable mass 92 is loaded, the rod 98 is able to move relative to the movable mass 92 through use of a two-stage hollow chamber 104. As shown in FIG. 14, the two-stage hollow chamber 104 is formed from the body of the movable mass 92 and includes a first relatively wide channel 106 generally positioned in front of a second relatively narrower channel 108. In general, the rod 98 is of a width or diameter that permits slide-through reception through both the first and second channels 106, 108. Moreover, the rod 98 is also of a length to at least partially remain in said slide-in engagement with the movable mass 92 between its unloaded position (FIGS. 9 and 13) and loaded position (FIGS. 10-12), including that the rod 98 is able to extend out from within the movable mass 92 (FIGS. 11-12) when the movable mass 92 is in the loaded position (FIGS. 10-12) and the pullback actuator 88 is in its normal resting position (FIGS. 9 and 11-13). The rod 98 further includes a selectively removable or permanent enlarged end 110 having a size and shape for slide-in reception within the relatively wider channel 106, but not the relatively narrower channel 108. As such, during loading, retracting the pullback actuator 88 causes the enlarged end 110 to contact a shoulder 112 where the relatively wider channel 106 transitions to the relatively narrower channel 108 within the movable mass 92. Such engagement within the two-stage hollow chamber 104 enables the pullback actuator 88 to retract the movable mass 92 within the barrel 94 and into compression against the internal compression spring 90 for eventual engagement with the trigger 86. In one embodiment, the internal compression spring 90 may be contained within the barrel 94 via at least one inwardly projecting retaining shoulder 114 (FIG. 14) wherein the internal compression spring 90 compresses between the movable mass 92 and one of more of these retaining shoulder(s) 114.

As illustrated best in FIG. 14, the trigger 86 downwardly projects from a trigger housing 116 coupled underneath the barrel 94. The trigger housing 116 further includes a trigger spring 118 contained within an enclosure 120 that upwardly biases a release lever 122 into an aperture 124 in the barrel 94. The movable mass 92 includes a commensurately sized notch 126 generally located near a back side 128 thereof; the mass 92 includes a chamfered edge 130 that facilitates engagement of the release lever 122 with the notch 126. That is, as the movable mass 92 retracts backwards, the chamfered edge 130 on the back side 128 of the movable mass 92 moves into contact with an upper chamfered edge 132 of the release lever 122. As such, the respective chamfered edges 130, 132 slide relative to one another, thereby placing a downward force on the upper chamfered edge 132, which causes the release lever 122 to push down on and to compress the trigger spring 118 underneath. Doing so allows the back side 128 of the movable mass 92 to continue moving until it extends beyond the release lever 122. Once beyond, the trigger spring 118 is able to push the release lever 122 into the notch 126 where the notch 126 retains the movable mass 92 in the loaded position, as illustrated, e.g., in FIGS. 10-12. As such, the release lever 122 projecting up into the notch 126 effectively prevents the compressed internal compression spring 90 from forcing the movable mass 92 forward down the barrel 94 and into contact with the impactor tip 24.

Once the movable mass 92 is locked, the surgeon may then slide the rod 98 of the pullback actuator 88 generally down the length of the barrel 94 to its normal resting position since the enlarged end 110 is of a size and shape to freely move out from within the relatively wide channel 106. Doing so allows the surgeon to operate the pullback actuator 88 relative to the movable mass 92 when loaded, without causing the movable mass 92 to disengage from its loaded position. The release lever 122, as best illustrated in FIG. 14, has a triangular base 134 generally extending into the enclosure 120 in the trigger housing 116. The trigger housing 116 includes a pair of sloped shoulders 136, 138 extending out and over a pair of opposing sloped sidewalls 140, 142 of the triangular base 134. Pulling the trigger 86, e.g., as shown in FIG. 12, causes the trigger housing 116 to slide forward wherein the sloped shoulder 138 moves into forward engagement with the sloped sidewall 142. Continued rearward movement of the trigger 86 continues forward sliding movement of the trigger housing 116 such that sloped engagement of the sloped shoulder 138 with the sloped sidewall 142 starts to apply a downward force on the release lever 122 as the sloped shoulder 138 slides along the sloped sidewall 142. Accordingly, this causes the release lever 122 to deflect downwardly, thereby applying a compressive force on the trigger spring 118 underneath. Upon full rearward movement of the trigger 86, the release lever 122 defects downwardly by a distance sufficient to retract out from within the notch 126 in the movable mass 92.

Once the release lever 122 disengages the notch 126, the movable mass 92 is no longer restrained in the loaded position. Here, the internal compression spring 90 is able to extend forward, thereby accelerating the movable mass 92 forward down the length of the barrel 94. Since the pullback actuator 88 is already in its normal forward resting position, releasing the movable mass 92 from the loaded position does not cause any further movement in the pullback actuator 88 as the movable mass 92 simply slides along the length of the rod 98. This may be particularly useful in preventing the handle 96 and/or the rod 98 of the pullback actuator 88 from catching on anything near the surgical opening (e.g., other surgical instruments, the surgeon's hands, etc.) during operation of the trigger-based hard liner removal instrument 22.

The trigger-based hard liner removal instrument 22 may further include an additional safety feature in the form of a trigger guard 144. As shown in FIG. 14, the trigger guard 144 may selectively couple to the trigger housing 116 via a pair of screws 146, 148. Once attached, the trigger guard 144 forms a cage surrounding or encompassing the trigger 86 to help prevent accidental actuation of the trigger 86 that may result in a misfire. Although, since the trigger-based hard liner removal instrument 22 is largely self-contained, any misfire would simply produce the aforementioned impulse 50 at the impactor tip 24 without any other consequence.

Figure 15:
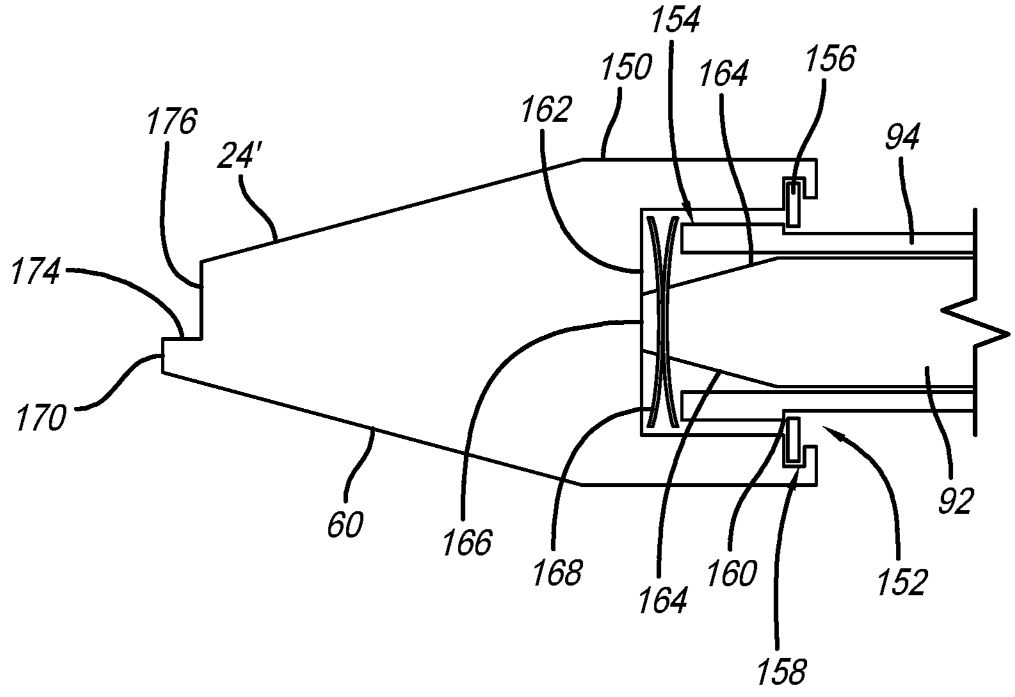
FIG. 15 is an enlarged perspective view taken about the circle 15 in FIG. 9, more specifically illustrating the impactor positioned over a front end of the barrel, and an outwardly projecting ledge for locating an impactor tip on the rim of the acetabular cup.

FIGS. 9-13 and 15 illustrate one embodiment wherein the trigger-based hard liner removal instrument 22 includes an impactor housing 150 designed to receive the movable mass 92, and subsequently translate the impulse 50 to the pulse 56 at the impactor tip 24 or 24' (FIG. More specifically, FIG. 15 illustrates that the impactor housing 150 includes an enclosure 152 having a size and shape for select reception of a front end 154 of the barrel 94. In this respect, the impactor housing 150 extends over the front end 154 of the barrel 94 and is retained thereover by a retaining clip 156 that at least partially extends into and is held within a cutout or groove 158 in the impactor housing 150. Furthermore, the barrel 94 includes a shoulder 160 that outwardly projects underneath the retaining clip 156 such that the front end 154 of the barrel 94 is captured between the retaining clip 156 and an inner wall 162 within the enclosure 152 of the impactor housing 150. As such, the retaining clip 156 effectively prevents the front end 154 of the barrel 94 from pulling out from engagement with the impactor housing 150.

FIG. 15 also illustrates that the movable mass 92 includes a tapered section 164 terminating in a strike point 166. An impact spring 168 may be located within the enclosure 152 between the inner wall 162 of the enclosure 152 and the front end 154 of the barrel 94. As the movable mass 92 accelerates down the length of the barrel 94 by way of the internal compression spring 90 applying a force thereto after activation by the trigger 86, the strike point 166 may contact the impact spring 168 and/or the inner wall 162, thereby creating the impulse 50. Furthermore, as the impactor housing 150 extends over the outside of the barrel 94, any air generated by the movable mass 92 traveling down the barrel 94 and/or striking the impact spring 168 and/or the inner wall 162 is forced out rearwardly from the enclosure 152 and away from the surgical opening. The impact spring 168 may have a thickness of about 1-5 mm, and be designed to soften the impact of the strike point 166 within the enclosure 152 of the impactor housing 150. As also illustrated in FIG. 15, the modified impactor tip 24' may include an outwardly projecting ledge 170 that may assist in locating the impactor tip 24' on a desired location (e.g., the rim 54 of the acetabular cup 28). For example, the surgeon may abut the ledge 170 against an outside surface 172 (FIG. 4) of the acetabular cup 28, thereby allowing the impactor tip 24' to rock forward into sitting engagement on the rim 54. This may help stabilize positioning of the impactor tip 24' on the rim 54 of the acetabular cup 28 by way of engagement of two surfaces, i.e., an inner surface 174 of the ledge 170 and a bottom surface 176 of the impactor tip 24'.

Figure 16:
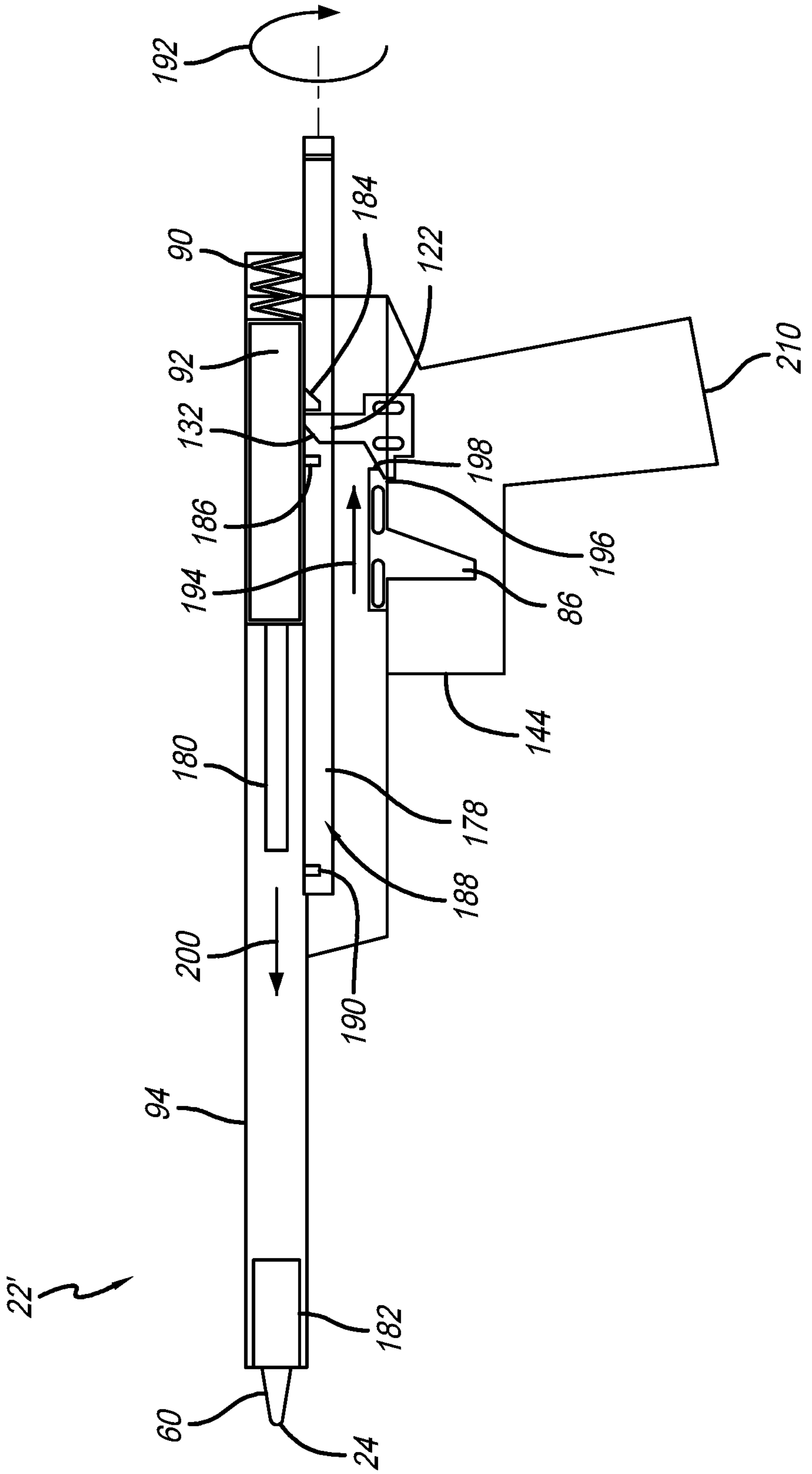
FIG. 16 is a perspective view of another alternative embodiment of a trigger-based hard liner removal instrument having a rotatable actuator that selectively engages the movable mass to pull the movable mass into the loaded position.

FIG. 16 illustrates an alternative embodiment of the trigger-based hard liner removal instrument 22' having a rotatable actuator 178 that operates movement of a strike post 180 within the barrel 94, which is designed to strike an internal impactor 182 to create the aforementioned impulse 50 at the impactor tip 24. In this embodiment, at least a portion of the internal impactor 182 may selectively or permanently couple to an inside of the barrel 94, whereby the taper 60 of the internal impactor 182 at least partially extends out therefrom and terminates into the impactor tip 24. The strike post 180 may extend out from a portion of the movable mass 92, as shown, or the strike post 180 may otherwise be formed integral with the movable mass 92.

Furthermore, FIG. 16 illustrates that the movable mass 92 includes a pair of downwardly extending projections, namely a rearwardly positioned chamfered projection 184 and a forwardly positioned projection 186. Each of the chamfered projection 184 and the loading projection 186 are of a size and shape to at least partially extend into a loading channel 188 formed from the rotatable actuator 178. As shown, the rotatable actuator 178 is coupled underneath the barrel 94, but the rotatable actuator 178 may also couple within the barrel 94 itself. In either embodiment, the rotatable actuator 178 can be clocked to reposition a retraction projection 190 in behind the loading projection 186 of the movable mass 92 for flush engagement therewith. As such, retracting the rotatable actuator 178 backwards then causes the retraction projection 190 now engaged with the loading projection 186 to retract the movable mass 92 within the barrel 94 against the internal compression spring 90. To load the trigger-based hard liner removal instrument 22', the rotatable actuator 178 retracts the movable mass 92 a distance sufficient to pull the chamfered projection 184 into contact with the upper chamfered edge 132 of the release lever 122. Here, continued rearward movement of the chamfered projection 184 along the interacting slope of the upper chamfered edge 132 places a downward force on an underlying spring (not shown), similar to that illustrated above with respect to the spring 118 of FIG. 14. Once the upper chamfered edge 132 clears the chamfered projection 184, the release lever 122 extends up between the chamfered projection 184 and the loading projection 186, as illustrated in FIG. 16. Here, after releasing the rotatable actuator 178, the internal compression spring 90 pushes the chamfered projection 184 forward into blocking engagement with the release lever 122, whereby the movable mass 92 remains retained in the loaded position. Here, the internal compression spring 90 remains substantially compressed within the barrel 94.

The surgeon may then rotate the rotatable actuator 178 clockwise along directional arrow 192 to disengage the retraction projection 190 from engagement with the loading projection 186. Although, of course, in alternative embodiments, the trigger-based hard liner removal instrument 22' may be configured such that the surgeon can rotate the rotatable actuator 178 counter-clockwise to release. The rotatable actuator 178 is then free to move along the length of the barrel 94 independent of the movable mass 92, e.g., for purposes of repositioning the rotatable actuator 178 back to the location illustrated in FIG. 16, without disrupting the movable mass 92' in the loaded position.

Thereafter, during actuation, the trigger 86 slides rearwardly along directional arrow 194 whereby a beveled shoulder 196 engages a sloped lip 198 of the release lever 122. Continued rearward movement of the trigger 86 causes the sloped lip 198 to slide along the beveled shoulder 196 and, as a result, to depress the release lever 122 downwardly. Eventually, the release lever 122 descends a distance sufficient to be removed out from within blocking relationship with the chamfered projection 184. Here, the internal compression spring 90 forcibly accelerates the movable mass 92 down the barrel 94 along directional arrow 200 until the strike post 180 strikes the internal impactor 182 to generate the aforementioned impulse 50.

Figure 17:
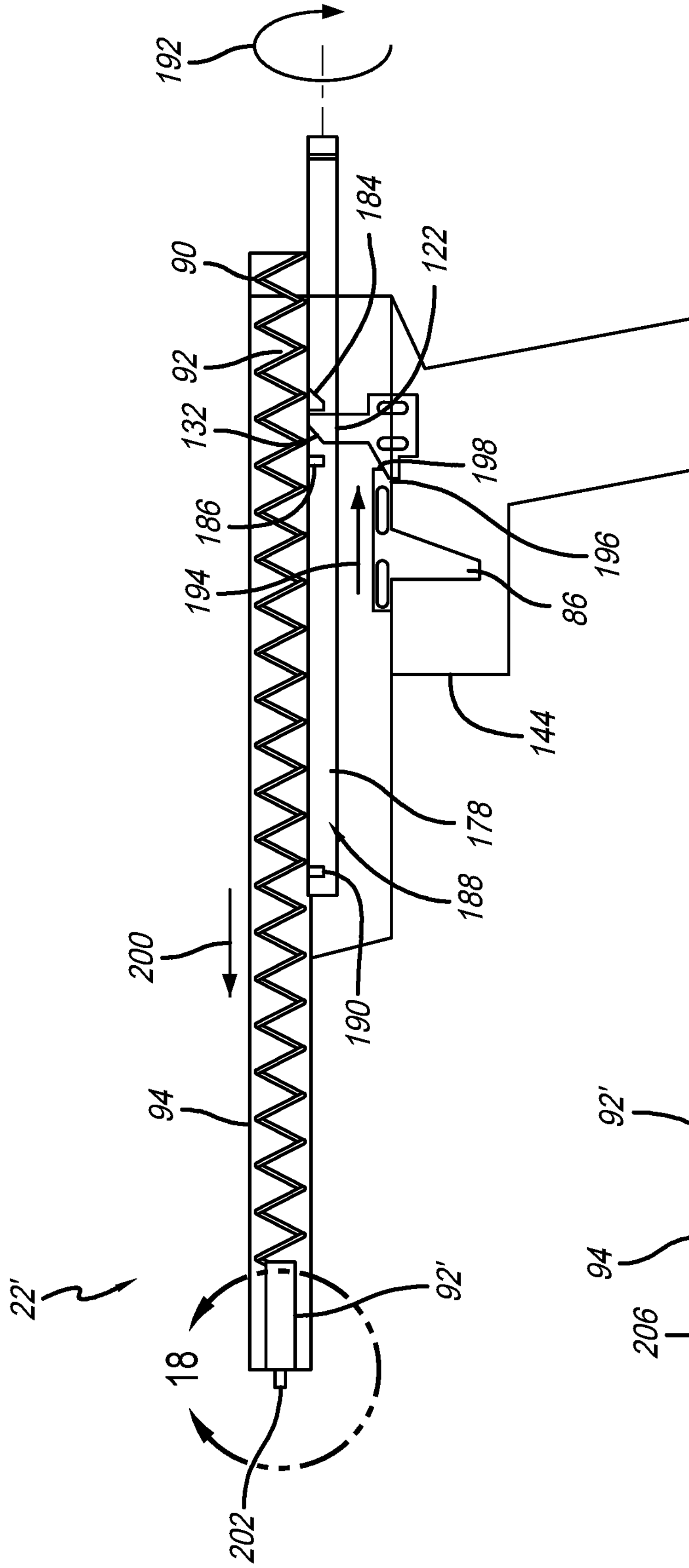
FIG. 17 is a perspective view of another alternative embodiment of a trigger-based hard liner removal instrument, including a movable mass selectively extendable out from within the barrel.
Figure 18:
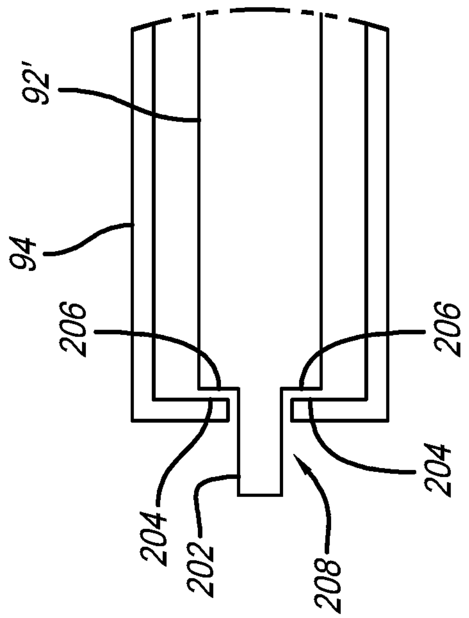
FIG. 18 is an enlarged perspective view taken generally about the circle 18 in FIG. 17, further illustrating the striking mass extending out from within the barrel.

In an alternative embodiment as illustrated in FIG. 17, instead of using the internal impactor 182, the trigger-based hard liner removal instrument 22' may include an alternative movable mass 92' designed to travel the length of the barrel 94 and extend out therefrom for direct contact to, e.g., a hardliner or acetabular cup for purposes of directly applying the aforementioned impulse 50. More specifically in this respect, when the release lever 122 descends a distance sufficient to be removed out from within blocking relationship with the chamfered projection 184, in this embodiment, the internal compression spring 90 forcibly accelerates the movable mass 92' down the entire length of the barrel 94 along directional arrow 200 until an impaction head 202 extends out from the barrel 94 and contacts an acetabular cup or hardliner. To ensure the movable mass 92' remains retained within the barrel 94 during use, the barrel 94 may include a pair of inwardly projecting stops 204 designed to interface with a respective pair of front shoulders 206 of the movable mass 92'. Here, as best illustrated in FIG. 18, the impaction head 202 is able to extend out from the barrel 94 through an end aperture 208 therein sized to accommodate slide through reception of the impaction head 202, but relatively smaller than the width of the respective front shoulders 206 such that the inwardly projecting stops 204 effectively prevent the movable mass 92' from being completely ejected out from within the barrel 94. As such, in this embodiment, the trigger-based hardliner removal instrument 22' is able to effectuate the impulse 50 to the acetabular cup or hardliner without the need for the impactor 40, the impactor housing 150, or the internal impactor 182.

As best illustrated in FIGS. 8 and 16, the trigger-based hard liner removal instrument 22, 22' may include a grip 210. The grip 210 may be ergonomically shaped to improve hand-manipulated comfort for the surgeon during surgery. Preferably, the grip 210 is of a size and shape to facilitate use with either the left or right hand, although, in alternative embodiments, the grip 210 of course may be designed for use with only one of the left hand or the right hand. One or more of the impactor tip 24, 24', the impactor 40, the handle 44, the striking mass 49, the pommel 74, the pinhead tip 82, the trigger 86, the barrel 94, the pullback actuator 88, the movable mass 92, the handle 96, the rod 98, the enlarged end 110, the trigger housing 116, the release lever 122, the triangular base 134, the trigger guard 144, the screws 146, 148, the impactor housing 150, the internal impactor 182, the strike post 180, the chamfered projection 184, the stopping projection 186, the rotatable actuator 178, and/or the grip 210 may be made out of a material suitable for repeat use and sterilization, such as a metal material (e.g., stainless steel, aluminum, titanium, or the like), a plastic material, and/or a biocompatible and high-density plastic material (e.g., polypropylene, polyethylene), or the like. Furthermore, the impactor tip 24, 24' may have a circular cross-section, square cross-section, triangular cross-section, or any shaped cross-section known in the art suitable for translating the pulse 56 to one or more of the components of the dual mobility acetabular prosthesis 26 pursuant to the embodiments disclosed herein.

Although several embodiments have been described in detail for purposes of illustration, various modifications may be made without departing from the scope and spirit of the invention. Accordingly, the invention is not to be limited, except as by the appended claims.

What is claimed is:

1. A hard liner removal instrument comprising:

a barrel containing a striking mass in slidable relation therewith;

a spring positioned between a first end of the barrel and the striking mass, the spring selectively movable between a normal resting position and a loaded position where the striking mass is positioned a greater distance from a second end of the barrel opposite the first end than when the spring is in the normal resting position, whereby movement of the spring from the loaded position to the normal resting position accelerates the striking mass into the second end of the barrel; and an externally accessible handle coupled with a rod extending generally coaxially through the spring and an aperture in the striking mass and terminating in a stopper relatively larger than the aperture in the striking mass;

wherein the striking mass includes a notch selectively slidably engageable with a spring-biased release lever;

wherein the release lever includes an outwardly flaring base slidably engaged with a pair of sloped shoulders extending thereover coupled to an externally accessible trigger.

2. The hard liner removal instrument of claim 1, wherein the spring comprises an internal compression spring positioned between the striking mass and at least one retaining shoulder inwardly projecting into the barrel.

3. The hard liner removal instrument of claim 2, wherein the internal compression spring comprises a size and shape to extend substantially along a length of the barrel when in the normal resting position.

4. The hard liner removal instrument of claim 1, wherein the aperture comprises a two-stage chamber including a first relatively wider channel having a size and shape to selectively receive the stopper therein in front of a second channel relatively smaller than the stopper while being of sufficient size and shape for passthrough reception of the rod.

5. The hard liner removal instrument of claim 4, wherein the first relatively wider channel and the second channel define a shoulder in between where the stopper seats when moving the spring from the normal resting position to the loaded position.

6. The hard liner removal instrument of claim 1, wherein the rod is selectively independently movable relative to the striking mass and selectively independently movable relative to the spring when the spring-biased release lever is selectively engaged with the notch of the striking mass.

7. The hard liner removal instrument of claim 1, including a trigger housing having a trigger spring normally biasing the release lever through an aperture in the barrel.

8. The hard liner removal instrument of claim 7, wherein the release lever includes a leading edge selectively slidable relative to a chamfered edge of the striking mass during movement of the spring from the normal resting position to the loaded position.

9. The hard liner removal instrument of claim 1, including an impactor housing having a groove selectively coupled with a retaining clip seated on an outwardly projecting step of the barrel.

10. The hard liner removal instrument of claim 9, wherein the impactor housing as a size and shape for select reception of a front end of the barrel.

11. The hard liner removal instrument of claim 10, including an impact spring seated within the enclosure between an inner wall thereof and the front end of the barrel.

12. The hard liner removal instrument of claim 11, wherein the impact spring comprises a thickness of 1-5 mm.

13. The hard liner removal instrument of claim 1, including an impactor housing positioned at the second end of the barrel.

14. The hard liner removal instrument of claim 13, wherein the impactor housing includes a tapered head having a tip forming an outwardly projecting ledge.

* * * * *